US012766041B2

(12) United States Patent
Church et al.

(10) Patent No.: US 12,766,041 B2
(45) Date of Patent: Oct. 20, 2026

(54) WEARABLE SENSOR

(71) Applicant: Sciperio, Inc, Orlando, FL (US)

(72) Inventors: Kenneth H. Church, Orlando, FL (US); Jon Mogford, College Station, TX (US)

(73) Assignee: Sciperio, Inc, Orlando, FL (US)

( * ) Notice: Subject to any disclaimer, the term of this patent is extended or adjusted under 35 U.S.C. 154(b) by 1257 days.

(21) Appl. No.: 17/583,741

(22) Filed: Jan. 25, 2022

(65) Prior Publication Data

US 2022/0241117 A1 Aug. 4, 2022

Related U.S. Application Data

(60) Provisional application No. 63/144,863, filed on Feb. 2, 2021.

(51) Int. Cl.
*A61F 13/04* (2006.01)
*A61H 23/02* (2006.01)
(Continued)

(52) U.S. Cl.
CPC ....... *A61F 13/041* (2013.01); *A61H 23/0245* (2013.01); *A61N 1/0492* (2013.01); (Continued)

(58) Field of Classification Search
CPC ................ A61H 23/00; A61H 23/0245; A61H 2201/165; A61H 2201/5058; (Continued)

(56) References Cited

U.S. PATENT DOCUMENTS

| | | | |
|---|---|---|---|
| 10,926,136 B1 | 2/2021 | Mogford et al. | |
| 11,327,443 B1 * | 5/2022 | Trapero Martin | G04B 37/1413 |

(Continued)

OTHER PUBLICATIONS

Dementyev, H.-L. C. Kao, J. Paradiso, "SensorTape: Modular and Programmable 3D-Aware Dense Sensor Network on a Tape", In Proc. of UIST 2015, 10 pages. www.artemdementyev.com/portfolio/sensor-tape.

(Continued)

*Primary Examiner* — Douglas Y Sul
(74) *Attorney, Agent, or Firm* — Goodhue, Coleman & Owens, P.C.

(57) ABSTRACT

A system includes a disposable patch having a first side and an opposite second side, the disposable patch having a body formed from a flexible material, a plurality of sensors positioned on the disposable patch, an electrically conductive pattern on the disposable patch wherein segments of the electrically conductive pattern are electrically connected to the plurality of sensors, and a reusable patch for positioning on the disposable patch, the reusable patch having a plurality of conductive connection points. The conductive pattern of the disposable patch and the conductive connection points of the reusable patch configured such that in an operative position the conductive connection points of the reusable patch are electrically connected to the conductive pattern
(Continued)

such that one or more electrical components of the reusable patch are electrically connected to the plurality of sensors of the disposable patch through the conductive pattern.

18 Claims, 8 Drawing Sheets

(51) Int. Cl.
*A61N 1/04* (2006.01)
*A61N 5/06* (2006.01)

(52) U.S. Cl.
CPC ...... *A61N 5/0616* (2013.01); *A61H 2201/165* (2013.01); *A61H 2201/501* (2013.01); *A61H 2201/5097* (2013.01); *A61N 2005/0626* (2013.01)

(58) Field of Classification Search
CPC .. A61N 1/0468; A61N 1/0464; A61N 1/0456; A61N 1/0452; A61N 1/0404; A61N 1/0492; A61N 2205/0626; A61B 5/14517; A61B 5/4277; A61B 5/4266; A61B 5/14514; A61B 5/685; A61B 5/6833
USPC .............................................................. 602/2
See application file for complete search history.

(56) References Cited

U.S. PATENT DOCUMENTS 12,178,579 B1 * 12/2024 Silver .................... A61B 5/746
2008/0139953 A1 * 6/2008 Baker .................... A61B 5/024 600/509
2008/0288026 A1 * 11/2008 Cross ................ H01R 13/5224 607/60
2013/0317333 A1 * 11/2013 Yang ................. A61B 5/02055 600/300
2015/0250422 A1 * 9/2015 Bay ...................... A61B 5/0533 600/391
2015/0335288 A1 * 11/2015 Toth ...................... A61B 5/388 600/391
2017/0281086 A1 * 10/2017 Donaldson ............ A61B 5/1118
2018/0125387 A1 * 5/2018 Hadley .................. A61B 5/259
2020/0101312 A1 * 4/2020 Pai ....................... A61N 5/0619

OTHER PUBLICATIONS

Kinesio Tape. https://kinesiotaping.com/about/what-is-kinesio-tape/. 4 pages. Date:N/A.
Xu S, Jayaraman A, Rogers JA. Skin sensors are the future of health care. Nature 2019; 571:319-21. 10.1038/d141586-019-02143-0 31316200.

* cited by examiner

WEARABLE SENSOR

RELATED APPLICATIONS

This application claims priority to U.S. Provisional Patent Application No. 63/144,863, filed Feb. 2, 2021, hereby incorporated by reference in its entirety.

FIELD OF THE INVENTION

The present invention relates generally to wearable devices. More particularly, but not exclusively, the present invention relates to wearable sensor device for use in applications such as therapeutics.

BACKGROUND

Health monitoring may be provided in a number of ways. A number of wearable devices have been developed and come in a variety of shapes and sizes and which provide health monitoring functionality. Watches, bands, and inserts are common as wearable devices. There are sensors in tape that are flexible to stick to diverse objects. One example of such technology is SensorTape and is described in A. Dementyev, H. L. C. Kao, J. Paradiso, "SensorTape: Modular and Programmable 3D-Aware Dense Sensor Network on a Tape", *In Proc. of UIST* 2015 and at www.artemdementyev.com/portfolio/sensor-tape. Skin sensors have also been developed that have electronics in a tape that sticks to the skin (see e.g. Xu S, Jayaraman A, Rogers J A. Skin sensors are the future of health care. *Nature* 2019; 571:319-21. 10.1038/d41586-019-02143-0 31316200 available at: https://www.nature.com/articles/d41586-019-02143-0).

Although seemly unrelated without having the benefit of this disclosure, kinesiology tape such as KINESIO TAPE is a therapeutic aid which is considered to reduce pressure while enabling a more effective flow of lymphatic fluid by taping a targeted area using a specially designed tape (see e.g. https://kinesiotaping.com/about/what-is-kinesio-tape/). Such tape is used as a therapeutic aid and then disposed of.

Despite the use of sensors in tape, problems may remain. For example, where complex electronics are present, incorporating electronics into disposable tape may be cost prohibitive. Therefore, what is needed is new and improved systems which may be used for health monitoring or other applications.

SUMMARY

Therefore, it is a primary object, feature, or advantage of the present invention to improve over the state of the art.

It is a further object, feature, or advantage is to provide for a system which can be digitally manufactured to accommodate a particular individual or a particular surface.

It is a further object, feature, or advantage of the present invention to provide therapeutic treatment.

It is a still further object, feature, or advantage of the present invention to provide therapeutic treatment in response to sensor measurements.

Another object, feature, or advantage is to enhance the use of kinesiology tape as a therapeutic aid.

Yet another object, feature, or advantage is to control actuation of piezo electrics for vibration, micropumps or other devices based at least in part on sensor data.

It is a further object, feature, or advantage of the present invention to provide a system with wearable sensors which includes a disposable portion and a reusable portion.

It is a still further object, feature, or advantage to provide for electrotherapy.

Another object, feature, or advantage is to provide a reusable patch which may be used with different disposable patches.

Yet another object, feature, or advantage is to provide a reusable patch which may include electronics, intelligent controls such as microcontrollers or processors, communications linkages, actuators, and sensors.

A further object, feature, or advantage is to provide a reusable patch which includes a reusable sticky portion to aid in sticking to a disposable patch.

A still further object, feature, or advantage is to provide a disposable patch with a sticky portion compatible with a reusable patch and a second sticky compatible with human skin.

Another object, feature, or advantage is to provide a disposable patch having sensors on it and an electrical pattern to connect to a reusable patch.

Yet another object, feature, or advantage is to provide a reusable patch that may connect to a second device wirelessly, such as, but not limited to, a smart phone.

A further object, feature, or advantage is to provide a software application such as a mobile app that translates raw data into quantifiable results for interpretation.

A still further object, feature, or advantage is to provide a reusable patch that may have actuation such as a piezo for vibration or a micropump.

Another object, feature, or advantage is to provide a reusable patch with electrodes to connect to a disposable patch that connects to the skin for electrotherapy.

Yet another object, feature, or advantage is to provide a reusable patch which includes a light source for light therapy.

A further object, feature, or advantage is to provide a reusable patch which communicates with an app through app connection to collect data from the reusable patch.

A still further object, feature, or advantage is to provide a reusable patch which communicates with an app through an app connection to receive data and commands.

One or more of these and/or other objects, features, or advantages of the present invention will become apparent from the specification and claims that follow. No single embodiment need provide each and every object, feature, or advantage. Different embodiments may have different objects, features, or advantages. Therefore, the present invention is not to be limited to or by any objects, features, or advantages stated herein.

According to one aspect, a system includes a disposable patch having a first side and an opposite second side, the disposable patch having a body formed from a flexible material, a plurality of sensors positioned on the disposable patch, an electrically conductive pattern on the disposable patch wherein segments of the electrically conductive pattern are electrically connected to the plurality of sensors, and a reusable patch for positioning on the disposable patch, the reusable patch having a plurality of conductive connection points. The conductive pattern of the disposable patch and the conductive connection points of the reusable patch configured such that in an operative position the conductive connection points of the reusable patch are electrically connected to the conductive pattern such that one or more electrical components of the reusable patch are electrically connected to the plurality of sensors of the disposable patch through the conductive pattern.

According to another aspect of the present disclosure, a method for monitoring includes attaching a disposable patch having a body formed from a flexible material to a surface, the disposable patch having a plurality of sensors positioned thereon and an electrically conductive pattern on the disposable patch and positioning a reusable patch on the disposable patch such that one or more electrical connections are made between the disposable patch and the reusable patch, the reusable patch having one or more electrical components in electrical communication with the plurality of sensors on the disposable patch.

According to one aspect of this disclosure, electronics are combined with kinesiology tape in order to provide therapeutic advantage. In conventional use, kinesiology tape such as KINESIO TAPE is an open loop approach. As described herein, through the use of electronics and sensors positioned to measure a number of physiological properties in localized and strategic areas provides methods to add pressure, electrical current, heat, and/or light for therapeutic healing. The sensing performed can include, without limitation, shock, vibration, temperature, moisture, pulse oximetry, or other properties or measurements.

According to another aspect, a method includes acquiring data about a patient and digitally manufacturing a device for fitting to the patient using the data about the patient, the device having a body, a plurality of sensors positioned on the body, and an electrically conductive pattern on the body wherein segments of the electrically conductive pattern are electrically connected to the plurality of sensors, an intelligent control operatively connected to the plurality of sensors, a wireless transceiver operatively connected to the intelligent control, and a therapeutic device in operative communication with the intelligent control, wherein the therapeutic device provides at least one of electro therapy, vibration, and light therapy. The method may further include fitting the device to the patient, sensing data using the plurality of sensors, and adjusting operation of the therapeutic device in response to the data. The data about the patient may include physical locations for placement of one or more of the plurality of sensors and the physical location for the therapeutic device. The body may be a brace body, sleeve, or other type of body.

BRIEF DESCRIPTION OF THE DRAWINGS

Illustrated embodiments of the disclosure are described in detail below with reference to the attached drawing figures, which are incorporated by reference herein.

DETAILED DESCRIPTION

A disposable patch and a reusable patch are used together. Such an approach addresses various problems associated with health monitoring. First, a therapeutic aid may have more efficacy where it can be custom fit to the body of an individual. Similarly, sensors may be able to be better placed when a device can be custom fit to the body of the individual. The disposable patch shown and described herein may be personalized and form fitted through digital manufacturing to target a specific area of the body of the individual as well as to physical connect with a reusable patch. The reusable patch may include electronics such as, but not limited to a microcontroller or other intelligent control, a communications linkage such as a radio transceiver such as a Bluetooth or BLE transceiver, power, and actuators.

Figure 1:
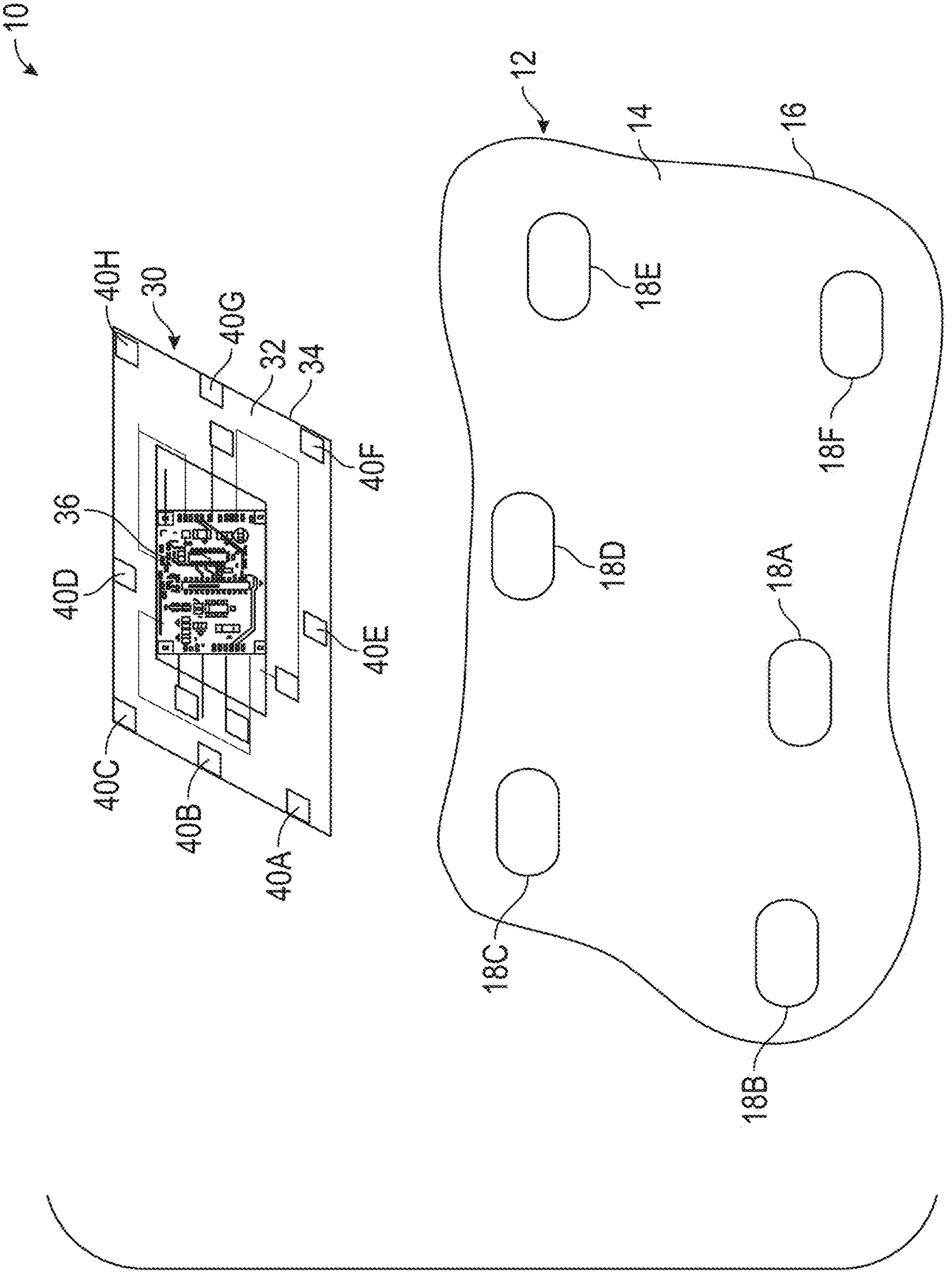
FIG. 1 illustrates a system which includes a reusable patch and a disposable patch.

FIG. 1 illustrates a system 10 of the present disclosure. The system 10 shown includes a disposable patch 12 which has a first side 14 and an opposite second side 16. There are a plurality of sensors 18A, 18B, 18C, 18D, 18E, 18F present on the disposable patch. It is to be understood that each of the sensors 18A-18F need not be a complete sensor unit. For example, in some embodiments one or more of sensors 18A-18F may be a contact point or pad area such as to make contact with a skin of an individual which is electrically connected to other aspects of the sensor. The disposable patch has a body formed from a flexible material such as that used for kinesiology tape or similar material. The disposable patch may thus be conformed such as to properly fit the body of a user so that sensors or other portions of the disposable patch 12 are positioned to allow for sensing desired parameters or for providing appropriate therapeutic effects. The disposable patch may be digitally manufactured to fit the body of a patient so that its size and placement of sensors allow the sensors to be positioned as desired.

The sensors 18A-18F may be used to sense shock, vibration, temperature, moisture, pulse oximetry or other parameters. It is to be understood that the parameters being sensed may be associated with physiological parameters such as skin temperature, skin conductivity, skin moisture, pulse oximetry, heart rate, or other types of physiological parameters. In other embodiments, the sensors 18A-18F may be used to sense other parameters such as where the disposable patch is attached to an object as opposed to a human or animal.

There is a reusable patch 30. The reusable patch 30 may have a top surface 32 and an opposite bottom surface 34. A number of conductive contact points 40A, 40B, 40C, 40D, 40E, 40F, 40G, 40H may be present. An intelligent control 36 such as a microcontroller or processor may be present as well as additional electronics which may include a wireless transceiver, battery or other power systems, signal conditioning circuitry, actuators, or sensors or portions thereof. The conductive contact points 40A-40H allow for electrically connecting sensors or sensor pad areas, contact points, or other portions of the disposable patch 12 to the reusable patch 30. The reusable patch 30 may have an adhesive on its bottom surface 34 to assist with adhering to or otherwise remaining in contact with the disposable patch 12. The disposable patch 12 may have an adhesive or other material on its opposite second side 16 to adhere to a person.

Figure 2:
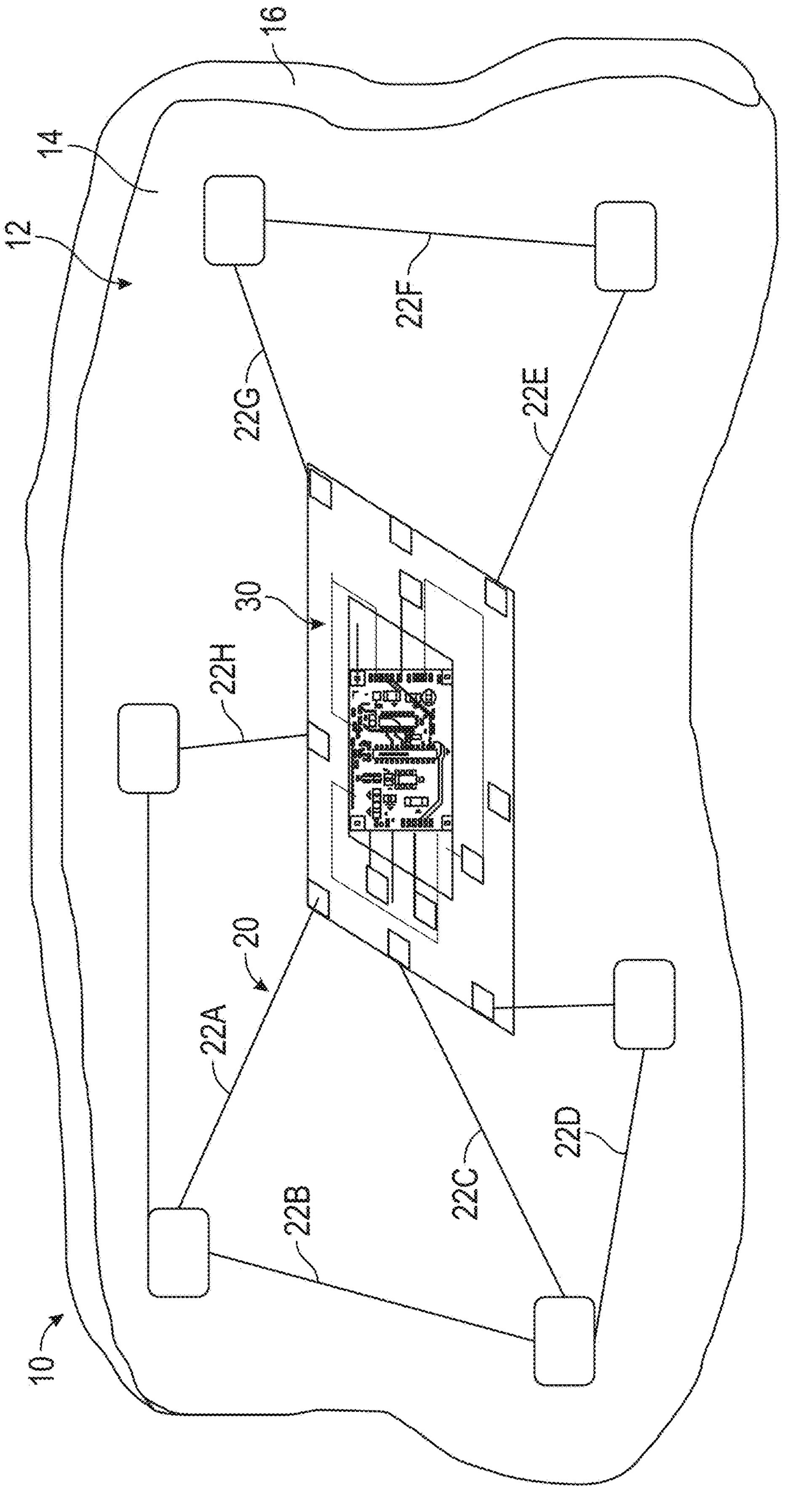
FIG. 2 illustrates the system where the reusable patch is attached to the disposable patch.

FIG. 2 illustrates the system 10 with the reusable patch 30 removably attached to the disposable patch 12. Note that as shown in FIG. 2, the disposable patch 12 also includes an electrically conductive pattern 20 which includes multiple portions or segments 22A, 22B, 22C, 22D, 22E, 22F, 22G, 22H. The electrically conductive pattern 20 provides for connecting portions of the disposable patch 12 such as sensors or contact points with one or more electronic components of the reusable patch 30.

Figure 3:
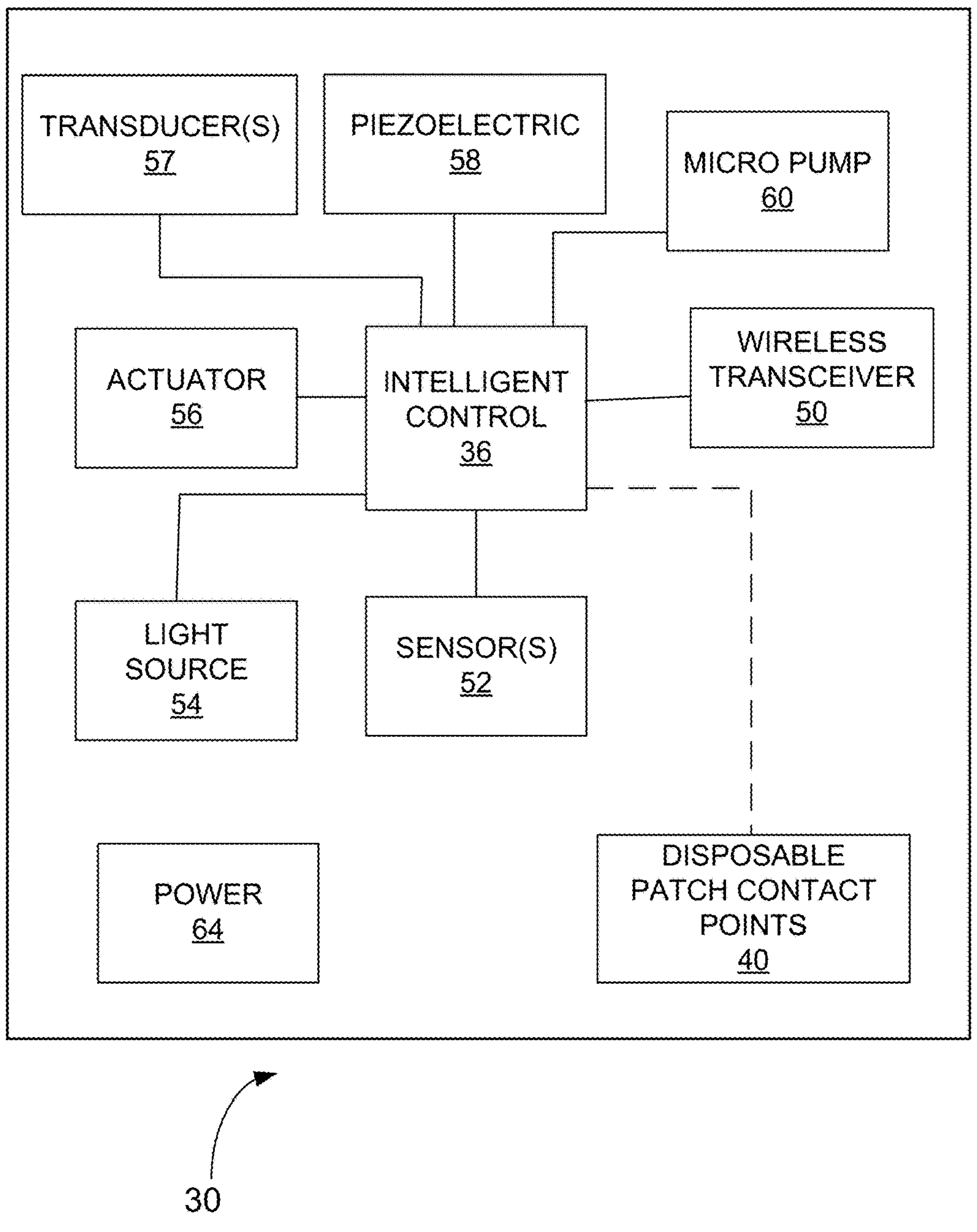
FIG. 3 is a block diagram illustrating one example of a reusable patch.

FIG. 3 is a block diagram illustrating one embodiment of the reusable patch 30. A shown in FIG. 3, the reusable patch 30 may have an intelligent control 36 such as a microprocessor or other processor. A communications link or linkage such as a wireless transceiver 50 may be operatively connected to the intelligent control 36. The wireless transceiver 50 may include an RF radio such as a Bluetooth radio or BLE. The wireless transceiver 50 may alternatively or additionally use ZigBee, near field communications (NFC), or may of other types which allow for communications between the reusable patch 30 and a remote device. One or more sensors 52 may also be operatively connected to the intelligent control 36. It is to be understood that although sensors 52 may be additionally positioned on the disposable patch, some sensors may be positioned on the reusable patch 30 itself and need not be positioned on the disposable patch. It is also to be understand that some sensors units may have portions on the disposable patch and portions on the reusable patch 30. Examples of sensors 52 may include environmental sensors such as ambient temperature sensors, humidity sensors, moisture sensors, light sensors, chemical sensors, gas sensors, or other types of sensors. Other sensors may include acoustic sensors, microphones, optical sensors, image sensors, inertial sensors, accelerometers, magnetometers, gyrometers, or other types of sensors.

Contact points 40 may be positioned at various locations on the reusable patch to facilitate electrical connection to one or more sensors or transducers on the disposable patch. Thus, the intelligent control 36 may be operatively connected to one or more sensors or transducers on the disposable patch.

Various types of actuators or other devices may also be present on the reusable patch 30 including components or devices that may be used to assist in providing therapeutic aid to an individual. For example, where present, the actuator 56 may be a vibration motor. Thus, the reusable patch 30 may provide therapeutic vibration where placed on an individual. A piezoelectric 58 which may be formed from a piezoelectric material may also be provided to provide therapy. For example, the piezoelectric may be energized in order to change shape in order to generate a vibration. A micropump 60 may be operatively connected to the intelligent control 36. The micropump 60 may be used to circulate a fluid. A light source 54 may also be operatively connected to the intelligent control 36. The light source 54 may be used to provide therapeutic light to an individual. For example, the light source 54 may be an infrared light source for providing infrared light therapy, however, any number of other types of light sources may be used. One or more transducers 57 may be present such as may be associated with electrical, acoustic, or other types of signals which may be used for therapeutic benefit.

A power subsystem 64 is also shown. The power subsystem may be used to provide power as needed for the reusable patch 30 as well as the disposable patch. The power system 64 may include one or more batteries or may provide for energy harvesting or otherwise produce or provide the desired energy requirements.

Figure 4:
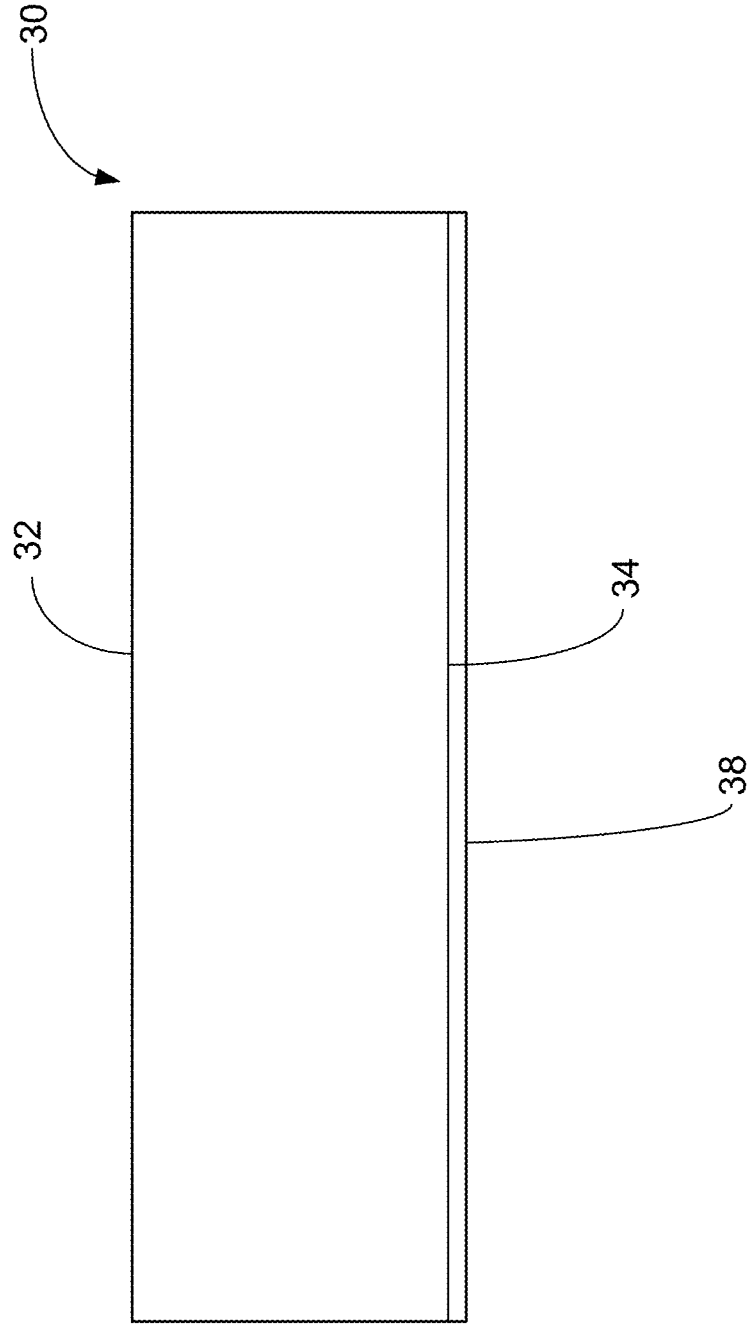
FIG. 4 is a side view of a reusable patch.

FIG. 4 is a side view of one example of the reusable patch 30. The reusable patch 30 includes a top surface 32 and a bottom surface 34. A material 38 may be placed on the bottom surface 34 to assist in attaching the reusable patch 30 to the disposable patch. It is contemplated that the material 38 may take various forms. It is also to be understood, that the top surface 32 and bottom surface 34 need not be level or even. For example, contact points (not shown) may extend lower than other portions of the bottom surface 34 to better facilitate contact with the disposable patch while still maintaining sufficient electrical contact.

Figure 5:
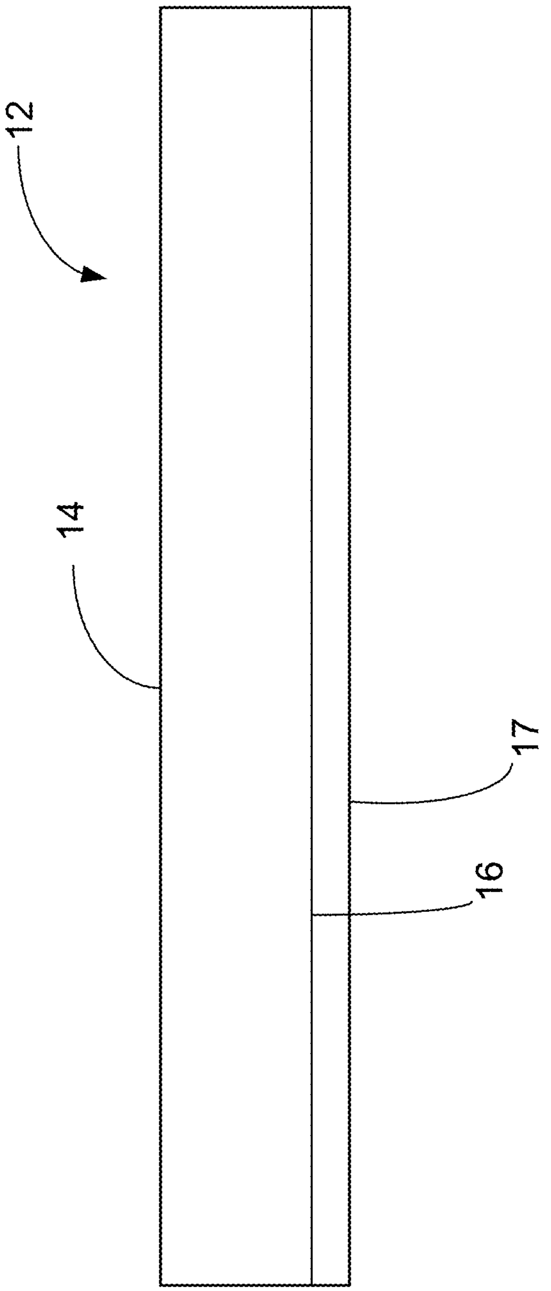
FIG. 5 is a side view of a disposable patch.

FIG. 5 is a side view of one example of the disposable patch 12 having a top surface 14 and a bottom surface 16 and may have an adhesive or other material 17 on the bottom side to promote contact between the disposable patch 12 and a patient or may be otherwise configured to attach to a patient. The disposable patch 12 may be made of a flexible and/or elastomeric material such as kinesiology tape. Adhesive material may also be present on the top surface 14 to attach to the reusable patch 30.

Figure 6:
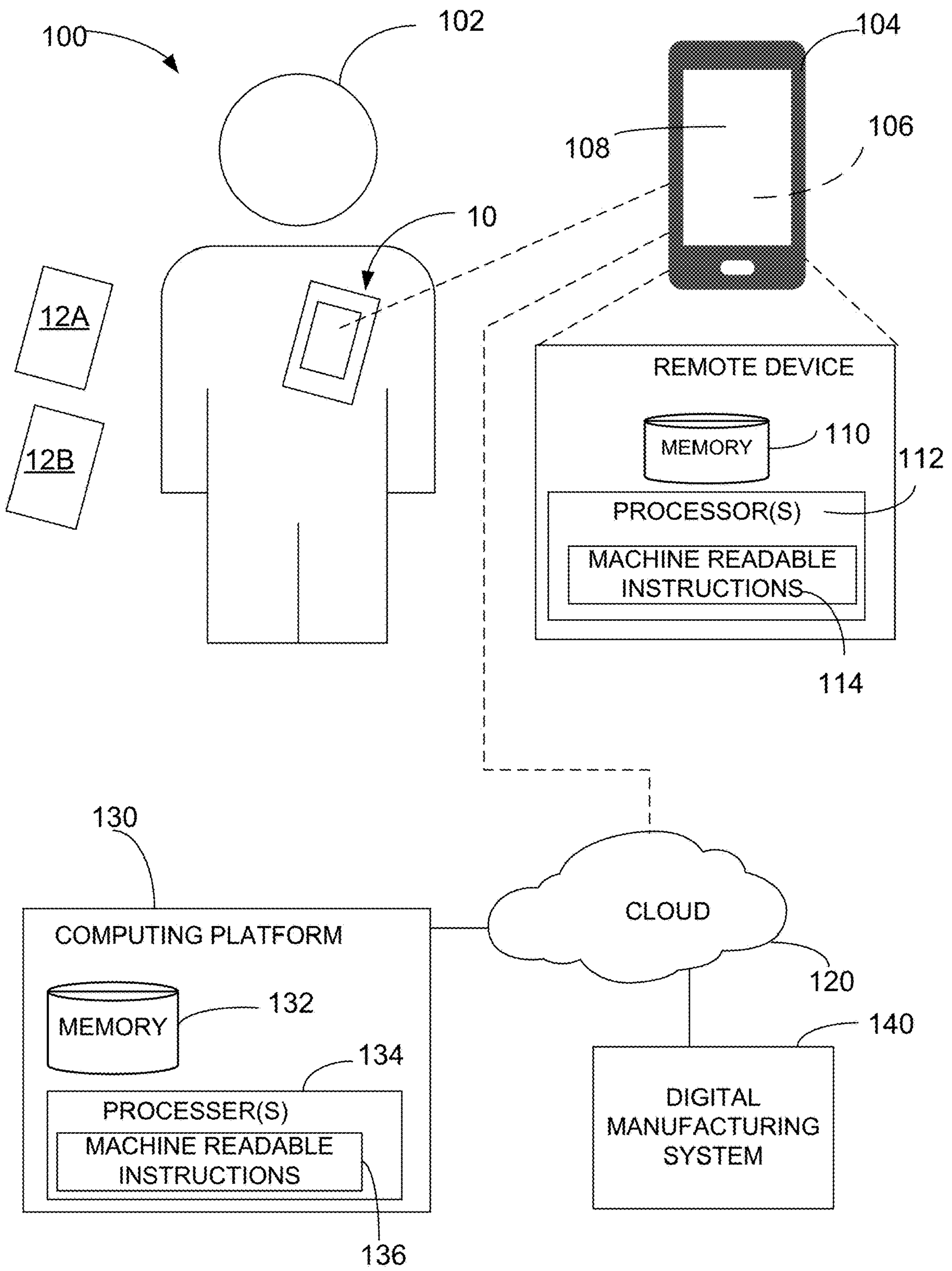
FIG. 6 is a pictorial representation of a system attached to an individual for health monitoring.

FIG. 6 further illustrates one example of a system 100 in use. As shown in FIG. 6, an individual or patient 102 is shown wearing a wearable system 10 which includes the reusable patch and the disposable patch. Additional disposable patches 12A, 12B are shown and the system 100 may further include one or more additional disposable patches 12A, 12B which may be used in combination with the reusable patch. In operation, sensor information may be communicated between the wearable system 10 and a remote device 104. The remote device 104 may take on any number of different forms. For example, the remote device 104 may be a mobile phone, tablet, computer, watch, or other smart wearable device. As shown, the remote device 104 is a mobile phone with a user interface including a display 108. The remote device further includes a memory 110 on which instructions for performing computing operations may be stored. The remote device may include one or more processor(s) 112. Machine readable instructions 114 may be performed by the one or more processors 112. The instructions may be formulated to perform various operations as shown and described herein such as to communicate to and/or from the wearable system 10 in order to provide command or control of the wearable system 10 to evaluate sensor data from the wearable system 10, to interact with the user interface 106 of the remote device 104 such as to display sensor data on a display 108 associated with the user interface 106, display results of the analysis, receive instructions from the user for modifying therapeutic actions based on the sensor data or otherwise.

The remote device 104 may also be in operative communication with a computing platform 130 such as provided by one or more servers or other computing platforms. The computing platform 130 may include a memory 132 and one or more processors 134. The computing platform 130 may also include machine readable instructions 136 for executing on the one or more processor(s) 134 for performing actions such as additional analysis of data. In some embodiments, it is contemplated that the computing platform 130 may provide access to other devices for modifying therapeutic actions. Thus, for example, a therapist or other health care provider could monitor effects of therapy on a patient and adjust therapeutic parameters based on observed data. Thus, a feedback loop may be established which is automatic or under partial or complete human control as may be appropriate in a particular application.

The computing platform 130 and remote device 104 are in operative communication over a network such as a cloud 120. A digital manufacturing system 140 is also shown in FIG. 6 which may include one or more 3D printing platforms or other digital manufacturing systems which may be used in fabricating the disposable patch. Thus, the disposable patch may be manufactured according to specifications of a particular individual or according to a layout for sensors area(s) or pad (areas) appropriate for a particular type of therapeutic intervention.

Figure 7:
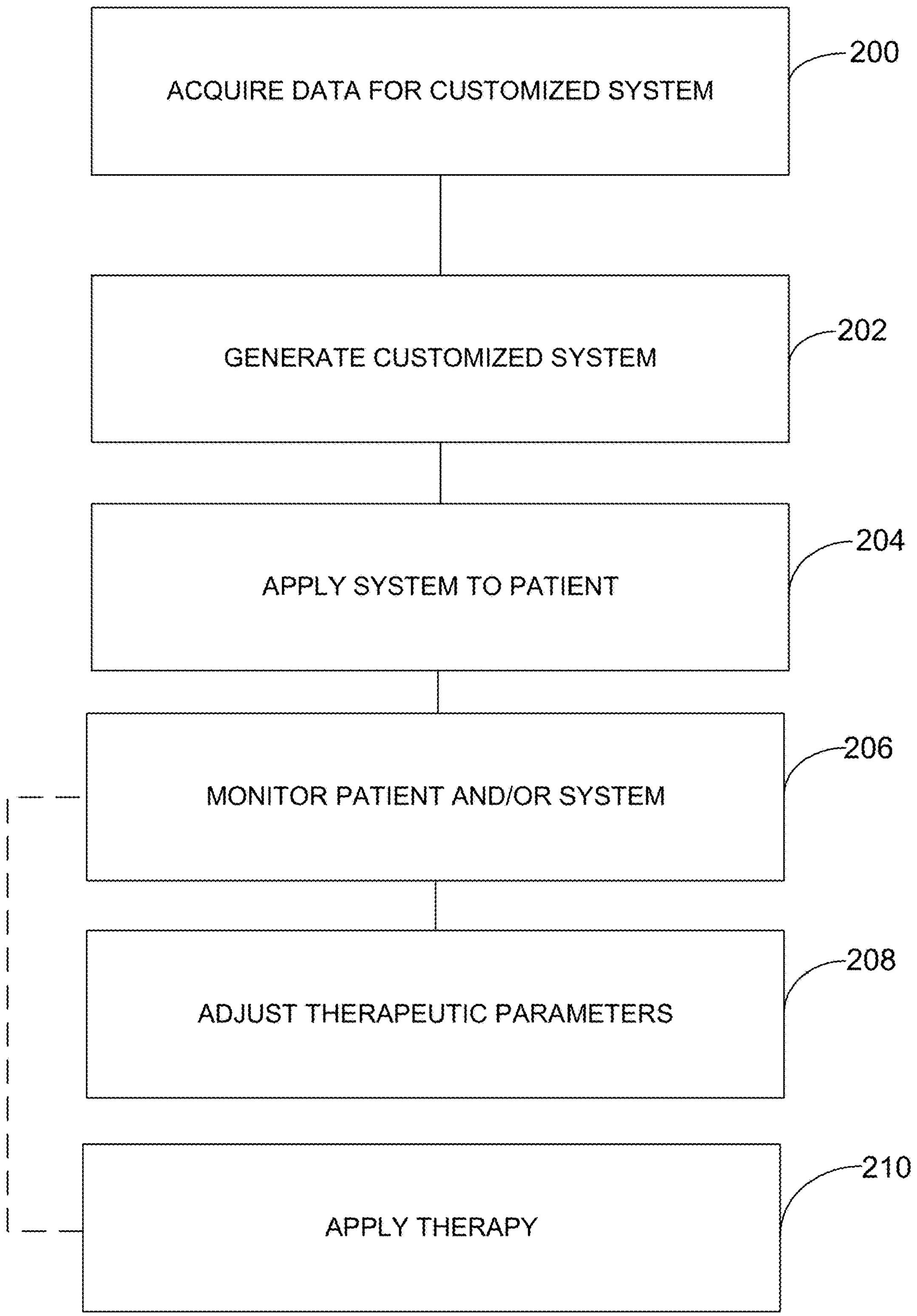
FIG. 7 is an example of a method for health monitoring.

FIG. 7 illustrates one example of a method which may be performed. In step 200, data is acquired for a customized wearable system. This data should be sufficient to define parameters needed to manufacture the disposable patch so as to customize the disposable patch for the individual and/or application. Such parameters may include dimensions used to define the size of the disposable patch, the number and location of sensors positioned on the patch, the size and position of conductive patterns as well as, in some embodiments, the type of materials, dimensions of the material, electrical requirements, or other parameters. In some embodiments, it is contemplated that this data may be acquired through acquiring image data for a patient for the area where the disposable patch is to be applied, and/or defining the purpose of the therapy or monitoring. In some embodiments, data for fabricating the disposable patch is acquired in a manner which is intuitive to health care professionals such as therapists, trainers, doctors, or others. Thus, there focus is on placement and the manner in which therapy is applied. For example, in some embodiments data for fabricating the disposable patch may be performed in whole or in part using a mobile device such as a mobile phone executing a mobile application. Thus, for example, images of the area of the body to be covered may be acquired using one or more cameras of the mobile device and photogrammetry methods may be applied to determine distances used in determining desired geometries for the disposable patch including placement of sensors. Additional data may be input by the user or therapist or otherwise acquired. It is also contemplated that a patient or user may provide the same information themselves in the same or similar manner.

Next, in step 202 a customized system is generated. In some embodiments this includes digital manufacturing of the disposable patch according to design specifications based on the data acquired in step 200. Thus, the disposable patch generated may include sensors or contact points for sensors positioned at desired locations. The disposable patch may also include an electrically conductive pattern where segments of the electrically conductive pattern are electrically connected to the sensors or contact points associated with the sensors. The disposable patch may include a portion similar in type, appearance, and function to physiotherapy tape.

In step 204, the system may be applied to a patient. Thus, for example, a disposable patch may be applied to a patient. The reusable patch may then be secured to the disposable patch such as through using adhesive or otherwise. The disposable patch should be applied so that sensors or contact points associated with sensors are positioned at desired locations on the body of the patient.

In step 206, the patient and/or the system may be monitored. The purpose of the monitoring may be to evaluate performance of the system and/or the effect of the system on the patient and/or physiological parameters associated with the patient. It is to be understood, that where multiple variables are present, any number of different models may be provided to assist in evaluating the parameters. For example, machine learning methods including neural networks may be used to evaluate. Based on data from monitoring the patient and/or system in step 206, in step 208 therapeutic parameters may be adjusted. Then in step 210 the therapy may be applied again and a feedback loop may be created which may lead to additional therapeutic parameter adjustments consistent with desired therapeutic results. In some embodiments evaluation of the data may be performed in whole or in part by the reusable patch and the intelligent control contained therein. In some embodiments, evaluation of the data may be performed in whole or in part by a remote device or at a remote server. It is further contemplated that quantified results may be provided to an individual such as a health care provider, trainer, therapist, or other individual or even the patient who may modify therapeutic parameters according to their analysis and desired outcomes.

For example, in some embodiments, vibration may be applied at particular areas in order to stimulate blood flow or for other therapeutic reasons. Ultrasound sensors may be used to assist in measuring blood flow to determine if the vibration applied provides sufficient stimulation of blood flow in a particular localized area. If not, then vibration frequency or amplitude or other parameters may be adjusted to increase stimulation.

By way of another example, heat may be applied at particular areas for therapeutic reasons such as with a heating element. Temperature sensors may be used to assist in measuring skin temperature to determine if the heat applied allows for skin temperature to meet the desired goal for therapeutic effect. If not, then more heat may be applied.

By way of another example, strain sensors may be present on the disposable patch and electrical impulses may provide therapy. The frequency and/or amplitude of the electrical impulses may be varied based on the strain sensed by the disposable patch.

By way of another example, skin conductivity may be measured, which may be used as an indicator of stress. This may be combined with other sensor measurements. For example, if therapy is creating too much stress for an individual then the amount of frequency of therapeutic interventions may be altered.

In step 208, therapeutic parameters may be modified or otherwise adjusted based on input or feedback obtained from step 206. These parameters may result in changes in heat applied, light applied, electricity, vibrations applied, motion applied, or result in other actions taken as may be appropriate in a particular application. Then in step 210 therapy may be applied based on the modified therapeutic parameters of step 208.

It is further to be understood that in some embodiments instead of both a reusable patch and a disposable patch a single patch may be used. Where a single patch is used, the patch may be digitally manufactured as previously described so that it may be precisely fit to a body of an individual or other specific object and sensors, actuators, and other components may be precisely placed. Where a single patch is used it is contemplated that additional electronic components may be present on the disposable patch so that the disposable match may include an intelligent control such as a processor or microcontroller in addition to one or more sensors, a wireless transceiver, or other components.

Figure 8:
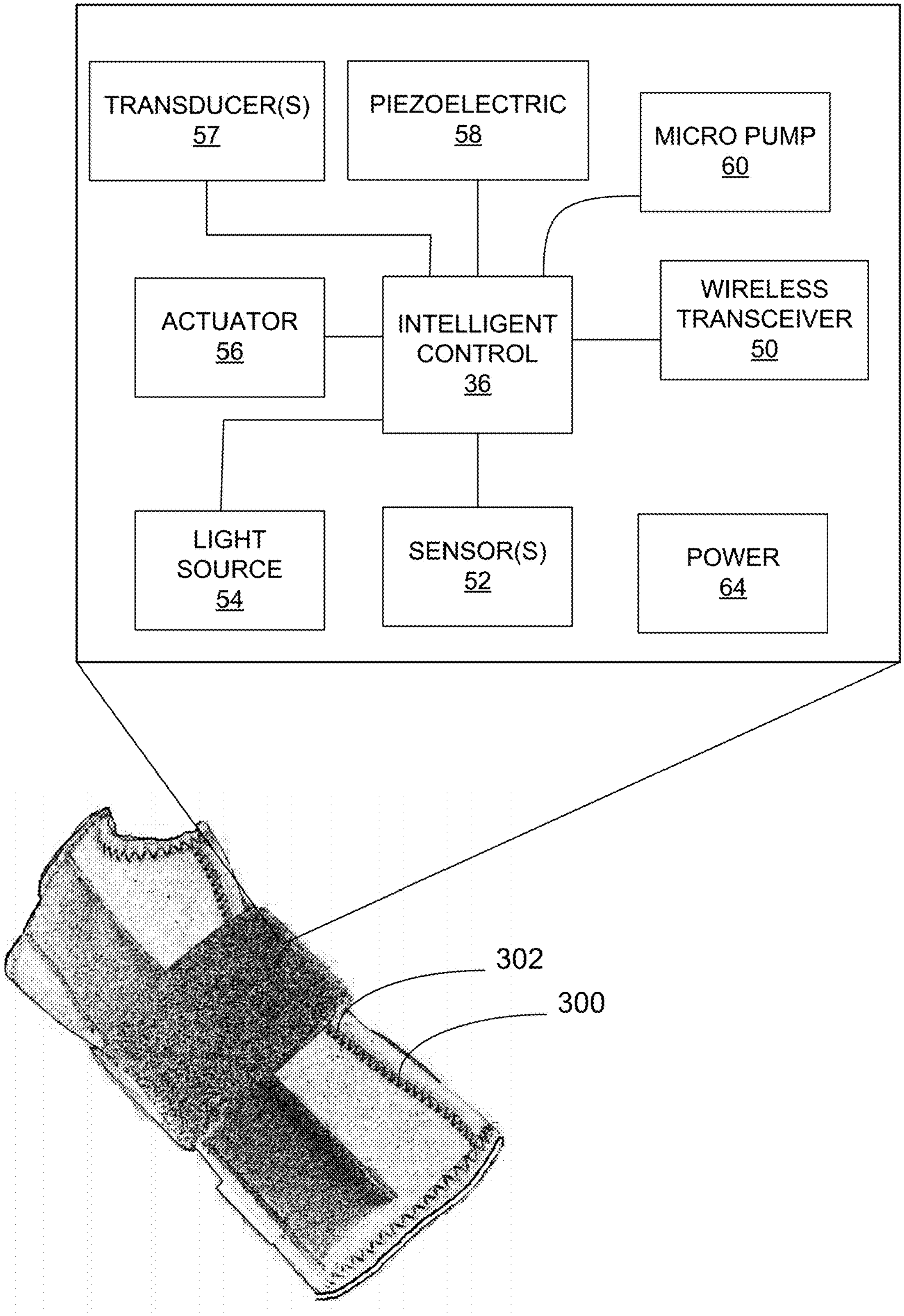
FIG. 8 illustrates the system incorporated into a brace.

FIG. 8 illustrates a device 300 which may be in the form of a brace for a patient such as a wrist brace, knee brace, or other type of brace, sleeve, or other body. The device 300 may include a brace body 302 for fitting to a patient. Fasteners such as hook and loop fasteners such as VELCRO may be present on the brace body 302. The device 300 or portions of the device may be digitally manufactured for fitting to a patient using data acquired about the patient such as in the manner previously expressed. This may include dimensions associated with a patient, desired locations for sensors and desired locations for therapeutic devices as well any other parameter which may be needed or helpful in manufacturing the device so that it may be best fit to a particular patient, to sense physiological or other parameters associated with the patient, or to deliver therapeutic aid to the patient.

As shown in FIG. 8, the device 300 may include an intelligent control 36, a wireless transceiver 50 operatively connected to the intelligent control 36. The intelligent control 36 may be a processor, microcontroller, or other type of intelligent control. A wireless transceiver 50 is also operatively connected to the intelligent control 36. One or more sensors 52 may be operatively connected to the intelligent control to provide for physiological monitoring, environmental monitoring, or to otherwise collect data for monitoring the patient, the environment, operation of the device, or other information which may be used to improve performance of the device or the therapy delivered by the device. One or more therapy devices may be operatively connected to the intelligent control which may include one or more light sources 54 for delivering light therapy to the patient, one or more transducers 57 for delivering electrotherapy to the patient, a piezo electric for delivering electrotherapy to the patient, an actuator 56 for delivering therapy through vibration or imparting movement to the patient, a micro pump 60 for delivering therapy to the patient, or other types of therapeutic devices.

Once the device 300 is manufactured according to the specifications associated with a patient, the device may be fitted to the patient such that the plurality of sensors are properly positioned and the one or more therapeutic devices are properly positioned. In some applications, the device 300 may be placed to provide therapy to a joint of a patient. In normal operation, data may be sensed using the plurality of sensors and the data may be analyzed either by the intelligent control 36 or remotely by sending the data to a remote device or location and receiving commands using the wireless transceiver 50. In response to analysis of the data, operation of the therapeutic device may be adjusted. The adjustments may include switching on or off the therapeutic device, adjusting the intensity of the therapy such as adjusting frequency of activation of an actuator or speed of an actuator, adjusting intensity of a light source, or otherwise adjusting operation of a therapeutic device.

Thus, it is to be understood that in some instances instead of attaching to a human body or other object using an adhesive, other forms of attachment may be used. For example, in some embodiments the sensors may be incorporated into a sleeve, brace, or other structure. All or portions of such a structure may be digitally manufactured. In some embodiments, a patch may be positioned within the sleeve, brace, or other structure by aligning the patch to a specified location of the sleeve, brace, or other structure. In such embodiments, the patch may be disposable and the sleeve, brace, or other structure may be reusable. In some embodiments, electronic components of a reusable patch may be associated with the sleeve, brace, or other structure.

It is to be understood that in some embodiments, the patient need not be a human but may be an animal. In addition, instead of the disposable patch being attached to a patient, it may also be attached to an inanimate object and may be used to measure and then control a localized area on the object. Where used in conjunction with an inanimate object then different sensors may be used. In some instances, instead of applying therapy, transducers or other components may be used to perform appropriate actions. For example, heat, sound, movement, and/or vibrations may be created as may be appropriate in a particular application or environment. The system may be used in any number of different applications including in manufacturing processes, in military applications, in space applications, especially where flexible and temporary solutions are needed to obtain sensor information and in some embodiments, provide for application of heat, light, vibration, electricity, magnetism, or motion in response to sensor information.

It is to be further understood that a feedback loop may be provided where sensors are used and control is imparted based on the sensor feedback. It is further to be understood that electronics and sensors may be used to measure a number of physiological properties in localized and strategic areas and providing a method to add pressure, electrical current, magnetism, heat or light for therapeutic healing or otherwise. Sensing can include, but is not limited to, shock, vibration, temperature, moisture, and pulse oximetry sensing.

It is to be further understood that the disposable patch may have low cost sensors that can be personalized and form fitted through digital manufacturing to target a specific area or localized area of a person, animal, or inanimate object. More complex sensors such as ultrasonic, imaging, chemical and biological sensors may be added.

Therefore, various methods, apparatus, and systems have been shown and described. Although specific embodiments are set forth herein, the present invention contemplates numerous different variations, options, and alternatives. It is to be further understood that different elements, components, or functions described herein may be combined with other elements, components, or functions described herein to expand system functionality or as may be appropriate for a particular application or environment. The invention is not to be limited to the particular embodiments described herein. The foregoing description has been presented for purposes of illustration and description. It is not intended to be an exhaustive list or limit any of the invention to the precise forms disclosed. It is contemplated that other alternatives or exemplary aspects are considered included in the invention. The description is merely examples of embodiments, processes, or methods of the invention. It is understood that any other modifications, substitutions, and/or additions can be made, which are within the intended spirit and scope of the invention.

What is claimed is:

1. A system comprising:

a disposable patch and a reusable patch formed based on a particular individual's data to accommodate the individual;

the disposable patch having a first side and an opposite second side, the disposable patch having a body formed from a flexible material, wherein the flexible material is kinesiology tape configured based on the particular individual's data as a therapeutic aid;

a plurality of sensors positioned, based on the particular individual's data, on the kinesiology tape of the disposable patch;

an electrically conductive pattern positioned, based on the particular individual's data, on the kinesiology tape of the disposable patch wherein segments of the electrically conductive pattern are electrically connected to the plurality of sensors;

the reusable patch for positioning on the disposable patch, the reusable patch having a plurality of conductive connection points;

the conductive pattern of the disposable patch and the conductive connection points of the reusable patch configured such that in an operative position the conductive connection points of the reusable patch are electrically connected to the conductive pattern on the disposable patch, such that one or more electrical components of the reusable patch are electrically connected to the plurality of sensors of the disposable patch through the conductive pattern to receive sensor data, and to provide therapeutic treatment in response to sensor data, wherein the physical location of one or more of the plurality of sensors on the kinesiology tape configured as a therapeutic aid is based on the individual's data.

2. The system of claim 1 further comprising at least one additional disposable patch for use with the reusable patch.

3. The system of claim 1 wherein the reusable patch includes a controller operative to process therapeutic data.

4. The system of claim 3 wherein the reusable patch further comprises a communications linkage.

5. The system of claim 4 wherein the reusable patch further comprises at least one actuator.

6. The system of claim 4 wherein the reusable patch further comprises at least one sensor.

7. The system of claim 1 wherein the reusable patch further comprises an adhesive or sticky portion for connecting to the disposable patch.

8. The system of claim 1 wherein the kinesiology tape further comprises a sticky portion compatible with a reusable patch and a second sticky portion compatible with human skin.

9. The system of claim 1 further comprising a second disposable patch, the second disposable patch having a body different in size or shape from the disposable patch, and wherein the reusable patch is configured for use with the disposable patch and use with the second disposable patch.

10. The system of claim 1 wherein the disposable patch further comprises a sticky portion for securing to a surface.

11. The system of claim 10 wherein the surface is human skin.

12. The system of claim 1 wherein the plurality of conductive connection points are positioned on the reusable patch based on the particular individual's data, and wherein the reusable patch further comprises an actuator.

13. The system of claim 12 wherein the actuator is selected from a set consisting of a piezo for vibration, a motor, and a micropump.

14. The system of claim 1 wherein the reusable patch further comprises at least one electrode for contact with skin of a patient to provide electrotherapy.

15. The system of claim 1 wherein the reusable patch further comprises a light source for providing light therapy.

16. The system of claim 1 further comprising a software application executing on a computing device and configured for communicating with the reusable patch using a wireless transceiver of the computing device.

17. The system of claim 16 wherein the software application translates raw data from the reusable patch into quantifiable results for interpretation and display to a user.

18. The system of claim 16 wherein the software application is configured to send data and commands to the reusable patch.

* * * * *